United States Patent [19]

Harris

[11] Patent Number: 5,015,753
[45] Date of Patent: May 14, 1991

[54] PROCESS FOR PREPARING POLY(ALKYLENE CARBONATE) MONOAHLS AND POLYAHLS USEFUL AS SURFACTANTS

[75] Inventor: Robert F. Harris, Midland, Mich.

[73] Assignee: The Dow Chemical Company, Midland, Mich.

[21] Appl. No.: 435,846

[22] Filed: Nov. 13, 1989

Related U.S. Application Data

[63] Continuation-in-part of Ser. No. 223,462, Jul. 22, 1988, Pat. No. 4,895,970, which is a continuation-in-part of Ser. No. 885,118, Jul. 14, 1986, abandoned.

[51] Int. Cl.$^5$ .............. C07C 69/96; C07C 261/00; C07C 69/00; C07G 269/00
[52] U.S. Cl. .................... 558/260; 560/115; 560/133; 560/135; 560/136; 560/137; 560/157; 560/159; 560/160; 560/161; 560/148; 560/165; 560/167; 558/275; 558/276; 558/277; 558/338; 558/404; 558/406; 558/408; 558/409; 558/410
[58] Field of Search ............. 560/115, 133, 135, 136, 560/137, 157, 159, 160, 161, 148, 165, 167; 558/260, 275, 276, 277, 338, 404, 406, 408, 409, 410

[56] References Cited

U.S. PATENT DOCUMENTS

| | | | |
|---|---|---|---|
| 3,332,980 | 7/1967 | Leary et al. | 558/248 |
| 3,632,828 | 1/1972 | Frevel et al. | 558/248 |
| 4,222,954 | 9/1980 | Cuscurida et al. | 558/248 |
| 4,330,481 | 5/1982 | Timberlake et al. | 558/248 |
| 4,353,834 | 10/1982 | Langdon | 558/248 |
| 4,382,014 | 5/1983 | Sakai et al. | 558/248 |
| 4,415,502 | 11/1983 | Timberlake et al. | 558/248 |
| 4,488,982 | 12/1984 | Cuscurida et al. | 558/248 |
| 4,504,418 | 3/1985 | Langdon | 558/248 |
| 4,686,273 | 8/1987 | Harris | 558/248 |
| 4,686,274 | 8/1987 | Harris et al. | 558/248 |
| 4,709,069 | 11/1987 | Harris | 558/248 |
| 4,745,162 | 5/1988 | Harris | 558/248 |
| 4,795,810 | 1/1989 | Harris | 528/370 |
| 4,816,529 | 3/1989 | Harris | 525/453 |

*Primary Examiner*—Mary C. Lee
*Assistant Examiner*—Robert C. Whittenbaugh

[57] ABSTRACT

Poly(alkylene carbonate) monoahls and polyahls useful as nonionic surfactants and having a poly(alkylene carbonate) backbone are prepared by reacting an oligomeric poly(alkylene carbonate) polyahl with a compound having mono- or difunctional active hydrogen moieties, such as alcohols, carboxylic acids, mercaptans, amides, primary or secondary amines, or substituted phenols, optionally in the presence of a catalyst, under transesterification conditions.

22 Claims, No Drawings

PROCESS FOR PREPARING POLY(ALKYLENE CARBONATE) MONOAHLS AND POLYAHLS USEFUL AS SURFACTANTS

CROSS-REFERENCE TO RELATED APPLICATION

This application is a continuation-in-part of 32,739A, Ser. No. 223,462, filed July 22, 1988, now U.S. Pat. No. 4,895,970 which is a continuation-in-part of 32,739, Ser. No. 885,118, filed July 14, 1986, now abandoned.

FIELD OF THE INVENTION

This invention relates to a method for preparing poly(alkylene carbonate) monoahls and/or polyahls useful as surfactants or functional fluids. This invention also relates to poly(alkylene carbonate) polyahls.

BACKGROUND OF THE INVENTION

Poly(alkylene carbonate) polyahls are randomized polymers containing a plurality of carbonate moieties, a plurality of active hydrogen moieties and di or higher polyalkyleneoxy units. An alkylene carbonate moiety is a repeating unit comprising an alkylene group bound to a carbonate moiety. Poly(alkylene carbonate) polyahls are known to be useful as surfactants.

Surfactants are compounds that reduce the surface tension when dissolved in water or water solutions, or which reduce the interfacial tension between two liquids, or between a liquid and a solid (see, for example, Nonionic Surfactants edited by M. J. Schick, Marcel Dekker, Inc., New York, 1967). Functional fluids are polyglycol-based fluids such as lubricants, hydraulic fluids, brake fluids, and compressor fluids (see, for example, *Kirk-Othmer* 12:719, ibidem., 18:633).

A variety of surfactants have been prepared by Langdon and described in a series of patents. U.S. Pat. No. 4,072,704 describes the coupling of polyethylene glycols and polypropylene glycols with either dialkyl carbonates or formaldehyde to give materials with surface-active properties. In U.S. Pat. No. 4,353,834 it is described how long-chain amides or sulfonamides have been coupled with hydrophilic polyglycols using dialkyl carbonates or esters of dicarboxylic acids to give materials with surface-active properties. This work was extended in U.S. Pat. No. 4,504,418 to include polyoxyalkylene polymers and monofunctional aliphatic, aromatic or aliphatic-aromatic alcohols coupled by alkyl carbonates or esters of dicarboxylic acids to give materials with surface-active properties.

U.S. Pat. No. 4,330,481 to Timberlake et al. describes the preparation of surfactants by reacting alcohols or alcohol ethoxylates with ethylene carbonate. These products are then further reacted with ethylene oxide to produce different surface-active materials as reported in U.S. Pat. No. 4,415,502. The preparation of surfactants and functional fluids by reacting alcohols, phenols or carboxylic acids (or their alkoxylated derivatives) with alkylene carbonates or alkylene oxides and carbon dioxide is described in U.S. Pat. No. 4,488,982 to Cuscurida.

U.S. Pat. No. 4,382,014 to Sakai et al. describes the preparation of surface-active materials by reacting alcohols, carboxylic acids or primary or secondary amines containing four or more carbon atoms or substituted phenols with alkylene carbonates in the presence of an ate-complex of a metal of Group II, III or IV of the Periodic Table having at least two alkoxy groups.

Low molecular weight polyoxyethylene glycol monomethyl ethers have been coupled using phosgene or alkyl carbonates to give materials useful in formulating brake fluids and as synthetic lubricants, as disclosed in U.S. Pat. No. 3,632,828. The coupling of monofunctional alcohols, phenols or their ethoxylated derivates using diphenyl carbonate to give surfactants is disclosed in U.S. Pat. No. 3,332,980.

Some poly(alkylene carbonate) polyahl nonionic surfactants of the general type produced by the method of the invention have been made by various procedures, including reacting alcohols with cyclic alkylene carbonates and reacting alcohols with alkylene oxides and carbon dioxide. However, before the present invention poly(alkylene ether carbonate) polyahls have never been used as the carbonate source in preparing carbonate-containing surfactants.

SUMMARY OF THE INVENTION

The present invention provides a novel process for preparing modified poly(alkylene carbonate) monoahls and/or polyahls which are nonionic surfactants and/or functional fluids containing a poly(alkylene carbonate) backbone.

According to this invention, poly(alkylene carbonate) polyahls are contacted with monoahls or diahls as hereinafter defined under conditions effective to form the modified poly(alkylene carbonate) monoahls and/or polyahls. Diahls which may be used include aliphatic diols, dicarboxylic acids, dimercaptans and primary diamines or secondary diamines. These difunctional compounds may have two different active hydrogen moieties, and include amino alcohols, amino acids, mercaptoalcohols, mercaptoacids and mercaptoamines. As a result of this modification, the active hydrogen moieties of the monoahl or diahl becomes bonded to the polyahl backbone to form products having molecular weights between, or intermediate to, those of the starting reactants.

The process of the invention may be used to produce materials which are useful as surfactants. The surfactant properties of the products, i.e., the modified poly(alkylene carbonate) monoahls and/or polyahls, can be varied by varying the molecular weight and the backbone structure of the poly(alkylene carbonate) polyahl, the length of the alkyl substituents on the monoahls and diahls, the type of active hydrogen moieties on the monoahls and diahls and the molar ratio of the reactants. Different surfactant compounds can be produced by further reacting the modified products with alkylene oxides or by first reacting the monofunctional or difunctional active hydrogen moieties with alkylene oxides before modification.

The carbonate backbone in the nonionic surfactants prepared by the present method can be degraded by bases, strong acids or by biodegradation. Accordingly, they will be degraded naturally and will not persist in the environment, which is an advantageous characteristic that is required by law in many localities.

DETAILED DESCRIPTION OF THE INVENTION

One of the starting materials for the process of the invention are poly(alkylene carbonate) polyahls, which are randomized polymers having a plurality of carbonate moieties, a plurality of active hydrogen moieties, and di- and higher polyalkyleneoxy units. An alkylene carbonate moiety is a repeating unit which has an alkylene group bound to a carbonate moiety. An active hydrogen moiety is a moiety containing a hydrogen atom which because of its position in the moiety displays significant activity according to the Zerewitinoff test described by Kohle, *J. Amer. Chem. Soc.*, 493181 (1927). Illustrative of such active hydrogen moieties are —COOH, —OH, —NH$_2$, —NH—, —CONH$_2$, —SH and —CONH—, although other reactive hydrogen-containing moieties may also be used. Alkyleneoxy moiety refers herein to a repeating unit which has an alkylene group bound to oxygen. Alkylene carbonate and alkyleneoxy moieties may be respectively represented by the following formulae:

$$+C(R^2)_2-C(R^2)_2-OCO+ \atop \| \atop O$$

and $$+C(R^2)_2-C(R^2)_2-O+$$

wherein $R^2$ is as hereinafter defined.

Preferred poly(alkylene carbonate) polyahls are random polyols represented by the formula:

$$R^1[X+C(R^2)_2C(R^2)_2O)_y-(C(R^2)_2C(R^2)_2OCQ\}_{\overline{x}} \quad (I)$$

$$+R^1(XA)_{n-1})_z-H]_n$$

wherein $R^1$ is separately in each occurrence an n-valent hydrocarbon radical or hydrocarbon radical which contains one or more heteroatoms of the group consisting of O, N and S;

$R^2$ is separately in each occurrence hydrogen, halogen, nitro, cyano, $C_{1-20}$ hydrocarbyl substituted with hydrogen or one or more of the group consisting of halo, cyano, nitro, thioalkyl, tert-amino, alkoxy, $C_{6-20}$ aryloxy, $C_{7-24}$ aralkoxy, carbonyldioxy($C_{1-20}$) alkyl, carbonyldioxy($C_{6-24}$) aryl, carbonyldioxy($C_{7-24}$) aralkyl, $C_{1-24}$ alkoxycarbonyl, $C_{6-24}$ aryloxycarbonyl, $C_{7-24}$ aralkoxycarbonyl, $C_{1-20}$ alkylcarbonyl, $C_{6-24}$ arylcarbonyl, $C_{7-24}$ aralkylcarbonyl, $C_{1-20}$ alkylsulfinyl, $C_{6-24}$ arylsulfinyl, $C_{7-24}$ aralkylsulfinyl, $C_{1-24}$ alkylsulfonyl, $C_{6-24}$ arylsulfonyl and $C_{7-24}$ aralkylsulfonyl;

X is separately in each occurrence S, O, NH, $$\begin{matrix} O & O & O \\ \| & \| & \| \\ -CO-, & -OCO-, & \text{or} & -OCNH-; \end{matrix}$$

A is separately in each occurrence $$+C(R^2)_2C(R^2)_2OCQ\}_{\overline{x}},$$

$$+C(R^2)_2C(R^2)_2O\}_{\overline{y}} \text{ or}$$

combinations thereof or a covalent bond;

Q is separately in each occurrence O, S or NH provided that all carbonate moieties are not terminal since terminal carbonate moieties are unstable and form OH moieties by elimination of $CO_2$;

n is separately in each occurrence an integer of from 1 to 25;

x is separately in each occurrence an integer of from 1 to 40;

y is separately in each occurrence an integer of from 1 to 120: and z is separately in each occurrence an integer of from 0 to 5.

A more preferred class of poly(alkylene carbonate) polyahls are poly(alkylene carbonate) polyols generally corresponding to the aforementioned formula wherein $R^1$, $R^2$ and n are as previously defined;

X is oxygen;

x is separately in each occurrence an integer of from 5 to 15; and z is an integer of from 0 to 2;

provided that the ratio of y to x is from 1:1 to 3:1.

In the hereinbefore-defined formulae, $R^1$ is preferably a $C_{1-24}$ aliphatic or $C_{6-24}$ cycloaliphatic hydrocarbon containing one or more oxygen, nitrogen or sulfur moieties; more preferably $R^1$ is an n-valent $C_{1-18}$ alkane or $C_{6-18}$ cycloalkene substituted with hydrogen or one or more oxygen, nitrogen or sulfur moieties; even preferably $R^1$ is an n-valent $C_{1-10}$ alkane substituted with hydrogen or one or more oxygen moieties.

$R^2$ is preferably hydrogen, $C_{1-20}$ alkyl, $C_{1-20}$ haloalkyl, $C_{1-20}$ alkenyl or phenyl: $R^2$ is more preferably hydrogen, $C_{1-3}$ alkyl, $C_{2-3}$ alkenyl, or phenyl; $R^2$ is even more preferably hydrogen, methyl or ethyl; $R^2$ is still more preferably hydrogen or methyl; and most preferably hydrogen.

X is preferably S, O or NH, and most preferably O. Preferably, n is an integer of 1 to 10, inclusive: more preferably, 1 to 5, inclusive: and most preferably n is 1 or 2.

For the purposes of this invention, it is understood that various hydrocarbon moieties such as alkyl, cycloalkyl, aryl, alkylene, acylene, etc., can be inertly-substituted with such moieties as halo, alkoxy, nitrile and other substituents which do not interfere with the modification reaction.

As used herein, the term "polyahl" includes any polyfunctional compound having on average more than one active hydrogen moiety as defined hereinbefore. Specifically included within the definition of polyahl are polyols, polyamines, polyamides, polymercaptans, polyacids and combinations thereof. However, other polymers containing active hydrogens as described hereinabove may also be used. Examples of polyahls suitable for use in the present invention may be found in U.S. Pat. No. 4,465,713 (column 2, line 42 through column 5, line 17), which is incorporated herein by reference.

Poly(alkylene carbonate) polyahl starting materials useful in this invention are prepared by any method known in the art, such as the condensation of an alkylene carbonate, carbon dioxide and an alkylene oxide, or mixtures of an alkylene carbonate, an alkylene oxide and/or $CO_2$, with an organic compound containing one or more active hydrogen atoms (initiator) in the presence of an alkaline catalyst or metal salt of an alkaline compound. Examples of these poly(alkylene carbonate) polyols and methods for preparation of these polyols are contained in U.S. Pat. Nos. 3,896,090 and 3,689,462 to Maximovich, U.S. Pat. No. 3,313,782 to Springmann, U.S. Pat. Nos. 3,248,416; 3,248,415 and 3,248,414 to Stevens and U.S. Pat. Nos. 4,686,273; 4,686,274 and 4,709,069 by the present inventor, which are all incorporated herein by reference. Alternatively, the poly(alkylene carbonate) polyahls can be prepared by reacting a dialkyl carbonate or diaryl carbonate with an initiator with two or more hydroxyl moieties (see, for example, U.S. Pat. No. 4,476,293 and U.S. Pat. No. 4,191,705, which are also incorporated herein by reference).

The other starting material, i.e., the modifier or modifying reactant, is a monoahl or a diahl. A "monoahl" is an organic compound having one active hydrogen moiety and a "diahl" is an organic compound having two active hydrogen moieties. When diamines are employed as the diahl, it is required that the amino moieties be separated by at least four carbon atoms to prevent unwanted intramolecular cyclization during modification of the poly(alkylene carbonate) polyahl. Although diamines having any number greater than 4 carbon atoms may be used, such as up to 30 and greater, preferred are those having up to 18 carbon atoms.

Examples of suitable monoahls include alcohols such as methanol, ethanol, propanol as well as phenols such as phenol, butylphenol, and methylnaphthol; primary and secondary monoamines such as butylamine, n-hexylamine, cyclohexylamine, 1-methylheptylamine, dodecylamine, n-butylaniline, tolyl-N-methylamine; mercaptans such as methyl mercaptan, ethyl mercaptan, dodecyl mercaptan and phenyl mercaptan: monoamides such as acetamide, fumaramide, acrylamide: carboxylic acids such as acetic acid and stearic acid and the like. Also suitable monoahls are adducts of alkylene oxide and alkyl phenols, alcohols and monocarboxylic acids such as those discussed in U.S. Pat. No. 4,488,982, which is also incorporated herein by reference. Of the monoahls, the alcohols, amines and mercaptans are preferred as modifying agents. However, other monoahls are also contemplated for use in the present invention.

Suitable exemplary diahls include alkylene glycols such as ethylene glycol and propylene glycol as well as poly(ethyleneoxy) glycols and poly(propyleneoxy) glycols and other alkane diols such as 1,6-hexane diol; and 1,4-butane diol. Diamines such as 1,6-diamino hexane and 1,12-diaminododecane, as well as other alkane diamines and dimercaptans such as dimercaptoethane and 1,12-dimercaptododecane, are also suitable diahls. In addition, diacids such as adipic acid and isophthalic and terephthalic acid are suitable, as are diamides such as 1,4-diamido butane, and bisphenols such as bisphenol A. Other suitable diahls such as diols, diacids and the like are described in U.S. Pat. No. 4,382.014, which is incorporated herein by reference. Of the diahls, the glycols, diamines and dimercaptans are preferred. It is also understood that mixtures of two or more monoahls, two or more diahls or at least one monoahl and at least one diahl can be suitably employed as the modifying reactant. It is further also understood that any monoahl, diahl or mixture thereof compatible with the present reactants may also be used in the practice of this invention.

In the preparation of surfactants, the modifying reactant preferably has at least one hydrophobic moiety which is sufficient to render the modified product surface active. Preferably, in such cases the modifying reactant shall have from about 8 to 20 carbon atoms, more preferably from 10 to 18 carbons.

Catalysts are preferably used in the modification of poly(alkylene carbonate) polyahls with the monoahls and/or diahls. These catalysts are advantageously known transesterification alkali metal or alkaline earth metal salt catalysts such as alkali metal hydroxides, alkaline earth metal hydroxides, alkali metal carbonates, alkaline earth metal carbonates, ammonium hydroxide, and ammonium carbonate. However, other salts of alkali metals or alkaline metals can also be used within the context of this invention.

Preferred catalysts for the modification (e.g., transesterification) of the poly(alkylene carbonate) polyahls are carbonates of metals such as lithium, sodium, potassium, rubidium, cesium, magnesium, calcium, strontium, barium, zinc, aluminum, titanium, cobalt, germanium, tin, lead, antimony, arsenic and cerium, as well as alkoxides thereof. Examples of other preferred catalysts are alkaline metal hydroxides, alkaline earth metal hydroxides, ammonium carbonates, alkaline metal borates, alkaline earth metal borates, ammonium borates, hydrocarbyloxy titanates, zinc borate, lead borate, zinc oxide, lead silicate, lead arsenate, litharge, lead carbonate, antimony trioxide, germanium dioxide, cerium trioxide, aluminum isopropoxide and titanium isopropoxide. Examples of other preferred catalysts include salts of organic acids of magnesium, calcium, cerium, barium, zinc and titanium, alkaline metal stannates, alkaline earth metal stannates, and ammonium stannates.

When amines are used as the modifying reactants, they can also function as the catalyst for the modification reaction. Thus, in many cases, an added catalyst does not provide any further advantage when an amine is used as the modifying reactant.

When a catalyst is employed, it is employed in an amount effective to promote the modification reaction at a rate sufficient to provide useful amounts of the modified poly(alkylene carbonate) polyahl within a 6-hour period. Preferably, the catalyst is employed in concentrations in the range from about 0.001 to about 2 weight percent, most preferably from about 0.1 to about 0.5 weight percent, based on the weight of total starting materials. Excessive amounts of catalyst are not favorable, particularly when used at high temperatures, since they often cause undesirable degradation of the poly(alkylene carbonate) polyahl.

Although the modification process of this invention may be carried out in an inert solvent such as acetone and methylene chloride, it is generally preferred to practice the process in the absence of solvents.

The modifying reactants, i.e., monoahl or diahl, are employed in amounts effective to provide the poly(alkylene carbonate) polyahl with the surface-active property when a surfactant is desired, or the required functional properties when a functional fluid is desired. Preferably, the modifying reactant is employed in an amount sufficient to provide an equivalent ratio of the ahl (mono or diahl) moiety of the modifying reactant to the carbonate moiety of the poly(alkylene carbonate) polyahl in the range from about 0.01:1 to about 2:1, more preferably from about 0.1:1 to 1:1, and still more preferably from about 0.2:1 to about 1:1.

The conditions, e.g., temperature and pressure used in the process of this invention are those effective to provide the desired modified product within a reasonable period, e.g., about 6 hours. An artisan can adjust the different conditions in accordance with the reactants employed and the specific characteristics of the random modified polymer desired. Preferably, the temperature is within the range from about 80° C. to 225° C., more preferably from about 125° C. to about 200° C., and most preferably from about 80° C. to about 175° C. In the case where an amine is employed as the modifying reactant it is desirable to use temperatures from about 80° C. to about 150° C. It is further observed that lower temperatures within the aforementioned ranges should be employed when higher concentrations of catalyst are used. These pressures may be employed in the practice of the present invention. While the pressures employed are most preferably about atmospheric, somewhat higher pressures are often desired when volatile solvents or volatile modifying reactants are employed.

The modified products of the process are recovered as is or can be obtained by extracting with solvents capable of dissolving either the modified product or the reactants but not both. By means of example, solvents for the various starting materials may be employed, which solvents are not solvents for the modified product. The converse is also possible. Solvents useful for the purification of the modified polyahls include liquid alkanes, alcohols and ketones.

The modified products of the process are generally defined as polymers (particularly oligomers) having ether and some carbonate moieties in the backbone of the polymer and the modifying reactant chemically bound to the polymer. While the carbonate moieties are virtually eliminated when very high ratios of the modifying reactant are employed, it is preferred to maintain an average of between about 0.5 to 10 carbonate moieties in each modified polymer molecule. Most preferably, the modified polymer molecule contains an average of from 1 to 5 carbonate moieties and about 1 chemically-bound reactant moiety per molecule.

Structurally, the modification of the poly(alkylene carbonate) polyahl with a monoahl at the site of reaction can be represented as follows

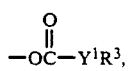

wherein

is the residue of the carbonate moiety

in the poly(alkylene carbonate) polyahl which has reacted with the monoahl HYR³ by removal of the active hydrogen moiety of the monoahl. In the above formula, R³ is a monovalent organic radical, preferably $C_{1-20}$ alkyl or $C_{1-20}$ cycloalkyl, $C_{6-24}$ aryl, $C_{7-24}$ aralkyl, ill more preferably $C_{1-18}$ alkyl.

$Y^1$ is O, S, NH or $NR^5$, wherein $R^5$ is $C_{1-4}$ alkyl.

In the case of a diahl ($HY^2R^4Y^2H$), the product at the site of reaction may be represented by the formula:

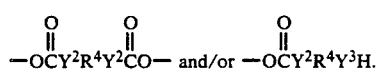

In the foregoing formulae, $R^4$ is a divalent organic radical, preferably a $C_{2-20}$ alkylene, $C_{2-20}$ cycloalkylene, $C_{6-24}$ arylene or $C_{7-24}$ aralkylene, still more preferably $C_{4-12}$ alkylene each $Y^2$ is independently O, S, NH or $NR^5$, preferably O, S and NH; and $Y^3$ is O, S, NH, $NR^5$ or

more preferably O, S and NH. $Y^1$, $Y^2$ and $Y^3$ are all the same and can be called $Y'$.

The entire structure of the modified polymer can thus be represented by substituting the aforementioned reacted carbonate moieties for all or a portion of the carbonate moieties of the poly(alkylene carbonate) polyahl polymer (Formula 1) given hereinabove.

As mentioned hereinbefore, it is desirable that only a portion of the carbonate moieties be reacted. Preferably, this portion is in the range from 10 to 90 weight percent, most preferably from about 25 to 50 weight percent, of the carbonate moieties of the initial poly(alkylene carbonate) polyahl.

ILLUSTRATIVE EMBODIMENTS

The following examples are included for illustrative purposes only, and are not meant to limit the scope of the invention or the claims. Unless otherwise stated, all parts and percentages are by weight.

The molecular weights and distribution are determined by size exclusion chromatography (SEC) on Waters Ultrastyragel © 1000 Å and 10,000 Å columns, arranged in series, using tetrahydrofuran (THF) as the mobile phase and calibrated with narrow molecular weight poly(ethylene glycol) standards using a refractive index detector.

EXAMPLE 1

Surfactant From n-Octanol and a Poly(ethylene carbonate) polyol Using a Carbonate:Hydroxyl Ratio of 1.9:1

A poly(ethylene carbonate) diol is prepared from monoethylene glycol and ethylene carbonate (27.6 percent $CO_2$; 0.00627 mole carbonate/g; 1943 molecular weight by hydroxyl titration).

A sample of this poly(ethylene carbonate) diol (20.00 g, 0.1254 mole carbonate) is combined with n-octanol (8.66 g, 0.0666 mole) and sodium stannate trihydrate (0.14 g, 0.5 percent) in a 50-ml, 3-necked flask equipped with overhead stirrer, condenser, thermometer, temperature controller and maintained under a nitrogen atmosphere. The flask is heated to 175° C. and samples are removed periodically for molecular weight determination by size exclusion chromatography (SEC). The results are contained in Table I hereinbelow.

TABLE I

| Sample Number | Conditions | Molecular Weight Data | | | |
|---|---|---|---|---|---|
| | | Peak | $\overline{M}n$ | $\overline{M}w$ | PDI |
| 1 | heated to 175° C. | 163 | 542 | 2558 | 4.71 |
| 3 | 30 min. at 175° C. | 163 | 487 | 1434 | 2.94 |
| 4 | 1 hour at 175° C. | 163 | 455 | 1293 | 2.84 |
| 5 | 1.5 hours at 175° C. | 973 | 431 | 901 | 2.09 |
| 6 | 2 hours at 175° C. | 795 | 429 | 825 | 1.93 |

Equilibrium is established in 1.5-2 hours. Comparative SEC values clearly show the progress of the reactions.

The product (27.2 g) is a pale straw-colored, low viscosity liquid.

The results of NMR analysis are as follows:
0.5-1.6 δ (multiplet, $CH_3(CH_2)_6-$, 1.0), 3.6-3.9 δ (multiplet, CH$_2$OCH$_2$—, 3.1),
4.0-4.5 δ (multiplet, CH$_2$OCO$_2$CH$_2$—, 1.9).

The product contains 19.7 percent CO$_2$ and 100 percent CO$_2$ is retained during reaction.

The surface tension is 35.8 dynes/cm (0.1 percent aqueous solution).

EXAMPLE 2

Surfactant From n-Octanol and a Poly(ethylene carbonate) polyol Using a Carbonate:Hydroxyl Ratio of 4.0:1

The same poly(ethylene carbonate) diol is used as in Example 1 above. A sample of this poly(ethylene carbonate) diol (20.00 g, 0.1254 mole carbonate) is combined with n-octanol (4.08 g, 0.0314 mole) and sodium stannate trihydrate (0.12 g, 0.5 percent) in the same apparatus used in Example 1 above. The flask is heated to 175° C. and samples are removed periodically for molecular weight determination by SEC. The results are contained in Table II hereinbelow.

TABLE II

| Sample Number | Conditions | Molecular Weight Data | | | |
|---|---|---|---|---|---|
| | | Peak | $\overline{M}n$ | $\overline{M}w$ | PDI |
| 1 | heated to 175° C. | 3020 | 680 | 2791 | 4.10 |
| 2 | 30 min. at 175° C. | 2461 | 645 | 2250 | 3.49 |
| 3 | 1 hour at 175° C. | 1806 | 600 | 1807 | 3.01 |
| 4 | 1.5 hours at 175° C. | 1628 | 599 | 1528 | 2.55 |
| 5 | 2 hours at 175° C. | 1468 | 571 | 1420 | 2.49 |
| 6 | 3 hours at 175° C. | 1324 | 542 | 1268 | 3.34 |
| 7 | 4.5 hours at 175° C. | 1195 | 571 | 1188 | 2.08 |
| 8 | 6 hours at 175° C. | 973 | 545 | 1117 | 2.05 |

Equilibrium is established in 3-4 hours. Comparative SEC values clearly show the progress of the reactions.

The product (20.4 g) is a pale straw-colored, low viscosity liquid.

The results of NMR analysis are as follows:
0.5-1.6 δ (multiplet, CH$_3$(CH$_2$)$_6$—, 1.0),
3.6-3.9 δ (multiplet, CH$_2$OCH$_2$—, 7.0),
4.1-4.5 δ (multiplet, CH$_2$OCO$_2$CH$_2$—, 4.2).

The product is 22.0 percent CO$_2$ and retains 9.65 percent CO$_2$.

The surface tension is 35.7 dynes/cm (0.1 percent aqueous solution).

EXAMPLE 3

Surfactant From n-Dodecanol and a Poly(ethylene carbonate) polyol Using a Carbonate:Hydroxyl Ratio of 2.5:1

The same poly(ethylene carbonate) diol is used as in Example 1 above. A sample of this poly(ethylene carbonate) diol (21.36 g, 0.1339 mole carbonate) is combined with n-dodecanol (9.98 g, 0.0536 mole) in the same apparatus used in Example 1 above. The flask is thoroughly flushed with nitrogen and 0.5 mg titanium isopropoxide is added as catalyst. The flask is heated to 175° C. and samples are removed after 30 minutes and 60 minutes at 175° C. The SEC values are contained in Table III hereinbelow.

TABLE III

| Sample Number | Conditions | Molecular Weight Data | | | |
|---|---|---|---|---|---|
| | | Peak | $\overline{M}n$ | $\overline{M}w$ | PDI |
| | starting material | 4086 | 1071 | 3623 | 3.38 |
| 1 | 30 min. at 175° C. | 535 | 471 | 906 | 2.17 |

TABLE III-continued

| Sample Number | Conditions | Molecular Weight Data | | | |
|---|---|---|---|---|---|
| | | Peak | $\overline{M}n$ | $\overline{M}w$ | PDI |
| 2 | 60 min. at 175° C. | 486 | 406 | 901 | 2.22 |

Equilibrium is established within 30 minutes at 175° C.

The product (31.3 g) is a straw-colored, low viscosity liquid.

The results of NMR analysis are as follows:
0.5-1.9 δ (multiplet, CH$_3$(CH$_2$)$_{10}$—, 1.0),
3.6-3.9 δ (multiplet, CH$_2$OCH$_2$—, 3.8),
4.0-4.5 δ (multiplet, CH$_2$OCO$_2$CH$_2$—, 2.5).

The product is 18.9 percent CO$_2$ and 100 percent CO$_2$ is retained during reaction.

The surface tension is 29.0 dynes/cm (0.1 percent aqueous solution).

EXAMPLE 4

Surfactant From n-Dodecylmercaptan and a Poly(ethylene carbonate) polyol Using a Carbonate:Mercaptan Ratio of 2.5:1

A poly(ethylene carbonate) polyol (Mn 1398) is prepared from ethylene carbonate and diethylene glycol. A sample of the poly(ethylene carbonate) polyol (18.82 g) is combined with n-dodecylmercaptan (9.32 g) using the same equipment of Example 1. These quantities represent a carbonate to mercaptan molar ratio of 2.5:1. The flask is thoroughly flushed with nitrogen and maintained under a nitrogen atmosphere. Titanium isopropoxide (0.5 ml) is added as catalyst and the contents of the reactor are heated to 175° C. Samples are removed periodically for molecular weight determination by SEC. The results are reported in Table IV hereinbelow.

Reaction is completed in 2 to 3 hours. Upon cooling to room temperature, two layers are present. The small upper layer containing some unreacted n-dodecylmercaptan is discarded.

TABLE IV

| Sample Number | Conditions | Molecular Weight Data | | | |
|---|---|---|---|---|---|
| | | Peak | $\overline{M}n$ | $\overline{M}w$ | PDI |
| 1 | heated to 175° C. | 168 | 503 | 1499 | 2.98 |
| 2 | 1 hour at 175° C. | 156 | 446 | 967 | 2.18 |
| 3 | 2 hours at 175° C. | 168 | 448 | 980 | 2.18 |
| 4 | 3 hours at 175° C. | 168 | 434 | 916 | 2.11 |
| 5 | 4 hours at 175° C. | 156 | 436 | 907 | 2.08 |

The lower product layer is a straw-colored, viscous liquid containing 19.5 percent CO$_2$ which displays the following characteristics:
Mn 429
Mw 979, and
PDI 2.28.

Proton-NMR data are consistent with the expected product.

Surface tension is 31.5 dynes/cm (0.1 percent aqueous solution).

EXAMPLE 5

Surfactant From n-Octadecylmercaptan and a Poly(ethylene carbonate) polyol made from Ethylene Oxide and Carbon Dioxide A poly(ethylene carbonate) polyol (Mn 2076; 27.4 weight percent CO$_2$) is prepared from ethylene oxide and carbon dioxide using diethylene glycol as initiator. A sample of the poly(ethylene carbonate) polyol (100.1 g) is combined with n-octadecylmercaptan (17.19 g) and sodium stannate trihydrate (0.59 g) in a 250-ml flask equipped with a condenser, thermometer, overhead stirrer and maintained under a nitrogen cover. The flask is heated to 175° C. and samples are removed periodically for molecular weight determination. The results obtained are shown in Table V hereinbelow.

TABLE V

| Sample Number | Conditions | Molecular Weight Data | | | |
|---|---|---|---|---|---|
| | | Peak | $\overline{M_n}$ | $\overline{M_w}$ | PDI |
| 1 | starting material | 4605 | 2076 | 4483 | 2.16 |
| 2 | 2 hours at 175° C. | 3484 | 1529 | 3402 | 2.23 |
| 3 | 3 hours at 175° C. | 3246 | 1479 | 3221 | 2.18 |
| 4 | 4 hours at 175° C. | 1895 | 1486 | 3080 | 2.07 |
| 5 | 5 hours at 175° C. | 1857 | 1457 | 2908 | 1.99 |

The product (113.5 g) is a white wax.
The results of NMR analysis are as follows:
0.7–1.6 δ (multiplet, $CH_3(CH_2)_{16}$—, 1.0),
3.4–3.9 δ (multiplet, $CH_2OCH_2$—, 30.4),
4.0–4.5 δ (multiplet, $CH_2OCO_2CH_2$—, 12.5).

Surface tension is 46.7 dynes/cm (0.1 percent aqueous solution: 23° C.).

EXAMPLE 6

Surfactant From n-Dodecylamine and a Poly(ethylene carbonate) polyol

A sample of the same poly(ethylene carbonate) polyol used in Example 5 (100.2 g) and n-dodecylamine (27.80 g) are combined in the same equipment used in Example 6. The flask is heated to 125° C. (no added catalyst) and samples are removed periodically for molecular weight determination. The results are listed in Table VI hereinbelow.

TABLE VI

| Sample Number | Conditions | Molecular Weight Data | | | |
|---|---|---|---|---|---|
| | | Peak | $\overline{M_n}$ | $\overline{M_w}$ | PDI |
| 1 | starting material | 4605 | 2076 | 4483 | 2.16 |
| 2 | 1 hour at 125° C. | 3214 | 1470 | 3147 | 2.14 |
| 3 | 2 hours at 125° C. | 2014 | 1187 | 2191 | 1.84 |
| 4 | 3 hours at 125° C. | 1515 | 1092 | 1848 | 1.69 |
| 5 | 4 hours at 125° C. | 1288 | 1051 | 1707 | 1.62 |
| 6 | 5 hours at 125° C. | 1288 | 1038 | 1668 | 1.61 |
| 7 | 6 hours at 125° C. | 1263 | 1019 | 1635 | 1.61 |

Reaction is completed with 3 to 4 hours.
The product (122.9 g) is a white wax: 0.189 meq amine/g, 83.9 percent amine conversion.
The results of NMR spectroscopic analysis are as follows:
0.7–1.6 δ (multiplet, $CH_3(CH_2)_{10}$—, 1.0),
3.3–3.9 δ (multiplet, $CH_2OCH_2$—, 9.7),
4.0–4.5 δ (multiplet, $CH_2OCO_2CH_2$—, 3.6).

Surface tension is 31.6 dynes/cm (0.1 percent aqueous solution: 23° C.).

This example shows that an amine can be used in the process of this invention. The amine also functions as a catalyst. Therefore, no additional catalyst is needed.

EXAMPLE 7

Surfactant From n-Hexadecylamine and a Poly(ethylene carbonate) polyol

A sample of the same poly(ethylene carbonate) polyol used in Example 5 (100.3 g) and n-hexadecylamine (19.33 g) are combined in the same equipment used in Example 6. The flask is heated to 125° C. and samples are removed periodically for molecular weight determination. The data are contained in Table VII hereinbelow.

TABLE VII

| Sample Number | Conditions | Molecular Weight Data | | | |
|---|---|---|---|---|---|
| | | Peak | $\overline{M_n}$ | $\overline{M_w}$ | PDI |
| 1 | starting material | 4605 | 2076 | 4483 | 2.16 |
| 2 | 2 hours at 125° C. | 4340 | 1952 | 4246 | 2.18 |
| 3 | 3 hours at 125° C. | 4089 | 1798 | 3940 | 2.19 |
| 4 | 4 hours at 125° C. | 4089 | 1798 | 3866 | 2.17 |
| 5 | 5 hours at 125° C. | 3775 | 1695 | 3509 | 2.20 |
| 6 | 6 hours at 125° C. | 3851 | 1657 | 3661 | 2.20 |

Reaction is completed with 4 to 5 hours.
The product (114.4 g) is a white wax: 0.0874 meq amine/g, 86.9 percent amine conversion.
The results of NMR spectroscopic analysis are as follows:
0.7–1.6 δ (multiplet, $CH_3(CH_2)_{14}$—, 1.0),
3.4–3.9 δ (multiplet, $CH_2OCH_2$—, 25.6),
4.0–4.5 δ (multiplet, $CH_2OCO_2CH_2$—, 10.7).

Surface tension is 44.1 dynes/om (0.1 percent aqueous solution: 23° C.).

EXAMPLE 8

Surfactant From 1,12-Diaminododecane and a Poly(ethylene carbonate) polyol

A sample of the same poly(ethylene carbonate) polyol used in Example 5 (100.5 g) and 1,12-diaminododecane (20.04 g) are combined in the same equipment used in Example 6. The flask is heated to 125° C. and samples are removed periodically for molecular weight determination. The results are tabulated below.

TABLE VIII

| Sample Number | Conditions | Molecular Weight Data | | | |
|---|---|---|---|---|---|
| | | Peak | $\overline{M_n}$ | $\overline{M_w}$ | PDI |
| 1 | starting material | 4605 | 2076 | 4483 | 2.16 |
| 2 | 1 hour at 125° C. | 1934 | 1046 | 2279 | 1.99 |
| 3 | 2 hours at 125° C. | 1974 | 1115 | 2223 | 1.99 |
| 4 | 3 hours at 125° C. | 2098 | 1152 | 2280 | 1.98 |
| 5 | 4 hours at 125° C. | 2098 | 1184 | 2348 | 1.96 |

The reaction is complete within one hour.
The product (116.6 g) is a white wax; 0.116 meq amine/g, 93.0 percent amine conversion.
The results of NMR spectroscopic analysis are as follows:
1.2–1.6 δ (singlet, –(CH$_2$)$_{10}$—, 1.0),
3.4–3.9 δ (multiple , $CH_2OCO_2CH_2$—, 5.3).

Surface tension is 52.2 dynes/cm (0.1 percent aqueous solution: 23° C.).

This example shows that an oleophilic diamine can be used in the process of this invention.

EXAMPLE 9

Surfactant From 1,10-Decanediol and a Poly(ethylene carbonate) polyol

A sample of the same poly(ethylene carbonate) polyol used in Example 5 (100.8 g), 1,10-decanediol (17.40 g) and sodium stannate trihydrate (0.59 g) are combined in the same equipment used in Example 5. The flask is heated to 150° C. and samples are removed periodically for molecular weight determination as described in Table IX.

TABLE IX

| Sample Number | Conditions | Molecular Weight Data | | | |
|---|---|---|---|---|---|
| | | Peak | $\overline{Mn}$ | $\overline{Mw}$ | PDI |
| 1 | starting material | 4605 | 2076 | 4483 | 2.16 |
| 2 | 1 hour at 150° C. | 2014 | 1175 | 2230 | 1.90 |
| 3 | 2 hours at 150° C. | 1974 | 1170 | 2241 | 1.91 |
| 4 | 3 hours at 150° C. | 2014 | 1179 | 2255 | 1.91 |

The reaction is complete within one hour.

The product (116.5 g) is a light straw-colored viscous liquid: Brookfield viscosity, 2570 cps at 23° C.

The results of NMR spectroscopic analysis are as follows:

1.2–2.0 δ (multiplet, $-(CH_2)_{10}-$, 1.0),
3.4–3.9 δ (multiplet, $CH_2OCO_2CH_2-$, 7.4).

Surface tension is 45.1 dynes/cm (0.1 percent aqueous solution: 23° C.).

This example shows that an oleophilic diol can be used in the process of this invention.

EXAMPLE 10

Surfactant From Lauric Acid and a Poly(ethylene carbonate) polyol

A sample of the same poly(ethylene carbonate) polyol used in Example 5 (100.5 g), lauric acid (24.04 g) and sodium stannate trihydrate (0.62 g) are combined in the same equipment used in Example 5. The flask is heated to 175° C. and samples are removed periodically for molecular weight determination. Table X contains a listing of the data obtained.

TABLE X

| Sample Number | Conditions | Molecular Weight Data | | | |
|---|---|---|---|---|---|
| | | Peak | $\overline{Mn}$ | $\overline{Mw}$ | PDI |
| 1 | starting material | 4605 | 2076 | 4483 | 2.16 |
| 2 | 1 hour at 175° C. | 350 | 1398 | 3822 | 2.73 |
| 3 | 2 hours at 175° C. | 3851 | 1414 | 3586 | 2.54 |
| 4 | 3 hours at 175° C. | 3700 | 1431 | 3416 | 2.39 |
| 5 | 4 hours at 175° C. | 3150 | 1402 | 3262 | 2.32 |

The reaction is complete within about 4 hours.

The product (120.2 g) is a light amber semi-solid. Size exclusion chromatography shows that the majority of the lauric acid has reacted.

The results of NMR spectroscopic analysis are as follows:

0.7–1.8 δ (multiplet, $CH_3(CH_2)_{10}-$, 1.0),
3.4–3.9 δ (multiplet, $CH_2OCH_2-$, 14.2),
4.0–4.5 δ (multiplet, $CH_2OCO_2CH_2-$, 5.8).

Surface tension is 31.2 dynes/cm (0.1 percent aqueous solution: 23° C.).

This example shows that an oleophilic acid can be used in the process of this invention.

It is understood that various other modifications will be apparent to, and can readily be made by, those skilled in the art without departing from the scope and spirit of this invention. Accordingly, it is not intended that the scope of the claims appended hereto be limited to the description as set forth herein, but rather that the claims be construed as encompassing all the features of patentable novelty that reside in the present invention, including all features that would be treated as equivalents thereof by those skilled in the art to which this invention pertains.

What is claimed is:

1. A process for preparing a modified poly(alkylene carbonate) monoahl and/or polyahl comprising contacting a poly(alkylene carbonate) polyahl represented by the formula:

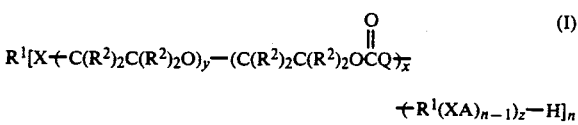

$$\overparen{+R^1(XA)_{n-1})_z-H]_n}$$

wherein

R[1] is separately in each occurrence an n-valent hydrocarbon radical or hydrocarbon radical which contains one or more heteroatoms of the group consisting of O, N and S;

R[2] is separately in each occurrence hydrogen, halogen, nitro, cyano, $C_{1-20}$ hydrocarbyl substituted with hydrogen or one or more of the group consisting of halo, cyano, nitro, thioalkyl, tert-amino, alkoxy, $C_{6-20}$ aryloxy, $C_{7-24}$ aralkoxy, carbonyldioxy($C_{1-20}$) alkyl, carbonyldioxy($C_{6-24}$) aryl, carbonyldioxy($C_{7-24}$) aralkyl, $C_{1-24}$ alkoxycarbonyl, $C_{6-24}$ aryloxycarbonyl, $C_{7-24}$ aralkoxycarbonyl, $C_{1-20}$ alkylcarbonyl, $C_{6-24}$ arylcarbonyl, $C_{7-24}$ aralkylcarbonyl, $c_{1-20}$ alkylsulfinyl, $C_{6-24}$ arylsulfinyl, $C_{7-24}$ aralkylsulfinyl, $C_{1-24}$ alkylsulfonyl, $C_{6-24}$ arylsulfonyl and $C_{7-24}$ aralkylsulfonyl;

X is separately in each occurrence S, O, NH, $$-\overset{O}{\overset{\|}{C}}O-,\ -O\overset{O}{\overset{\|}{C}}O-,\ \text{or}\ -O\overset{O}{\overset{\|}{C}}NH-;$$

A is separately in each occurrence

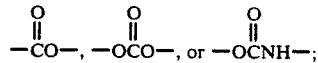,

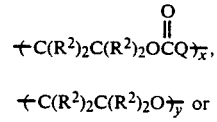 or combinations thereof or a covalent bond;

Q is separately in each occurrence O, S or NH provided that all carbonate moieties are not terminal since terminal carbonate moieties are unstable and form OH moieties by elimination of $CO_2$;

n is separately in each occurrence an integer of from 1 to 25;

x is separately in each occurrence an integer of from 1 to 40;

y is separately in each occurrence an integer of from 1 to 120; and z is separately in each occurrence an integer of from 0 to 5;

a monoahl represented by the formula $HY^1R^3$ or a diahl represented by the formula $HY^2R^4Y^2H$, wherein $Y^1$ and $Y^2$ are O, S, NH or $NH^5$, wherein $R^5$ is $C_{1-4}$ alkyl; $R^3$ is a $C_{1-20}$ alkyl or $C_{1-20}$ cycloalkyl, $C_{6-24}$ aryl, or $C_{7-24}$ aralkyl; and $R^4$ is $C_{2-20}$ alkylene, $C_{2-20}$ cycloalkylene, $C_{6-24}$ arylene or $C_{7-24}$ aralkylene, under conditions effective to form the modified poly(alkylene carbonate) monoahl and/or polyahl.

2. The process of claim 1 which is conducted at a pressure of about one atmosphere, and wherein a transesterification catalyst is employed.

3. The process of claim 1 which is conducted at a temperature between about 80° C. and 225° C.

4. The process of claim 3 which is conducted at a temperature between about 125° C. and about 200° C.

5. The process of claim 1 wherein the monoahl is selected from the group consisting of an aliphatic alcohol, a carboxylic acid, an amide, a mercaptan, a $C_{4-24}$ primary amine, a $C_{4-24}$ secondary amine, and phenol substituted with $C_{1-18}$ alkyl.

6. The process of claim 5 wherein the monoahl is a $C_{4-18}$ primary or secondary amine.

7. The process of claim 5 wherein the monoahl is a phenol substituted with one to four $C_{1-12}$ alkyl moieties.

8. The process of claim 1 wherein the monoahl is a linear alcohol selected from the group consisting of hexanol, octanol, decanol, dodecanol, tetradecanol, hexadecanol, octadecanol, and mixtures thereof.

9. The process of claim 8 wherein the linear alcohol is n-octanol or n-dodecanol.

10. The process of claim 1 wherein the diahl is an oleophilic compound selected from the group consisting of aliphatic diols, aliphatic mercaptans, aliphatic diamines, aliphatic dicarboxylic acids, and aliphatic compounds containing two different substituents selected from the group consisting of hydroxyl, amine, mercaptan, and carboxylic acid.

11. The process of claim 2 wherein the transesterification catalyst is an alkoxide or a carbonate selected from the group consisting of alkoxides or carbonates of alkali metals, alkaline earth metals, and titanium.

12. The process of claim 11 wherein the transesterification catalyst is an alkoxide or carbonate of sodium or potassium.

13. The process of claim 11 wherein the transesterification catalyst is an alkoxide of titanium.

14. The process of claim 13 wherein the transesterification catalyst is titanium isopropoxide.

15. The process of claim 2 wherein the transesterification catalyst is selected from the group consisting of alkali metal stannates, alkaline earth metal stannates, and ammonium stannates.

16. The process of claim 15 wherein the transesterification catalyst is sodium stannate or potassium stannate.

17. The process of claim 1 wherein the modified poly(alkylene carbonate) polyahl has a molecular weight between the molecular weights of the reactants.

18. The process of claim 2 wherein the monoahl or diahl is an amine and also functions as a transesterification catalyst.

19. The process of claim 1 further comprising reacting the modified poly(alkylene carbonate) polyahl with an alkylene oxide.

20. The process of claim 1 wherein mono- or diahl is reacted with an alkylene oxide prior to the modification step.

21. The process of claim 5 wherein the poly(alkylene carbonate) polyahl is reacted with a monoahl selected from the group consisting of aliphatic mercaptans, cycloaliphatic mercaptans, and aryl mercaptans.

22. The process of claim 21 wherein alkylene oxide and carbon dioxide are substituted for the poly(alkylene carbonate) polyahl, and the mercaptan is alkyl mercaptan.

* * * * *